US00PP32085P2

(12) United States Plant Patent
Schoustra

(10) Patent No.: US PP32,085 P2
(45) Date of Patent: Aug. 18, 2020

(54) LILAC PLANT NAMED 'SCHOLIROFRAG'

(50) Latin Name: *Syringea hybrida*
Varietal Denomination: SCHolirofrag

(71) Applicant: John Schoustra, Somis, CA (US)

(72) Inventor: John Schoustra, Somis, CA (US)

( * ) Notice: Subject to any disclaimer, the term of this patent is extended or adjusted under 35 U.S.C. 154(b) by 0 days.

(21) Appl. No.: 16/602,343

(22) Filed: Sep. 18, 2019

(51) Int. Cl.
*A01H 5/02* (2018.01)
*A01H 6/00* (2018.01)

(52) U.S. Cl.
USPC ..... Plt./248

(58) Field of Classification Search
USPC ..... Plt./248
CPC ..... A01H 6/00; A01H 5/02
See application file for complete search history.

*Primary Examiner* — Keith O. Robinson
(74) *Attorney, Agent, or Firm* — Barbara Campbell; Cochran Freund & Young LLC

(57) ABSTRACT

A new and distinct variety of lilac plant having an upright, dense, deciduous shrub which can be trained as a small tree and lilac-colored flowers having a very strong lilac scent, is disclosed.

2 Drawing Sheets

Genus and species: *Syringea hybrida.*
Denomination: 'SCHohrofrag'.

BACKGROUND

'SCHolirofrag' is a new and distinct variety of lilac. 'SCHolirofrag' originated from a controlled cross in April 2008 in Somis, Calif. between the female parent, an un-named and unpatented lilac seedling having lilac-colored flowers, and the commercial male parent, 'Snowy Beach Party' (unpatented).

The resulting seeds from the cross were collected in August 2008 and planted and evaluated in Somis, Calif. 'SCHolirofrag' was selected in April 2012 from the population of seedlings in Somis, Calif. 'SCHolirofrag' was first asexually propagated in April 2014 in Somis, Calif. from two node softwood cuttings rooted under mist at 25 to 27 degrees Celsius. In 2016, 'SCHolirofrag' was subsequently propagated via tissue culture and micro-propagation.

Other subsequent asexual propagations were conducted in controlled environments in Somis, Calif. and Tipp City, Ohio and demonstrate that 'SCHolirofrag' reproduces true to type in successive generations of asexual reproduction via softwood cuttings, tissue culture, and mirco-propagation.

SUMMARY

The following are the most outstanding and distinguishing characteristics of this new variety when grown under normal horticultural practices in Somis, Calif. and Tipp City, Ohio.

1. An upright, dense, deciduous shrub which can be trained as a small tree; and
2. Lilac-colored flowers having a very strong lilac scent.

DESCRIPTION OF THE PHOTOGRAPHS

This new lilac plant is illustrated by the accompanying photographs which show the plant's overall plant habit including form, foliage, and flowers. The photographs are of a 3-year old plant grown outdoors in Tipp City, Ohio. The colors shown are as true as can be reasonably obtained by conventional photographic procedures.

Figure 1:
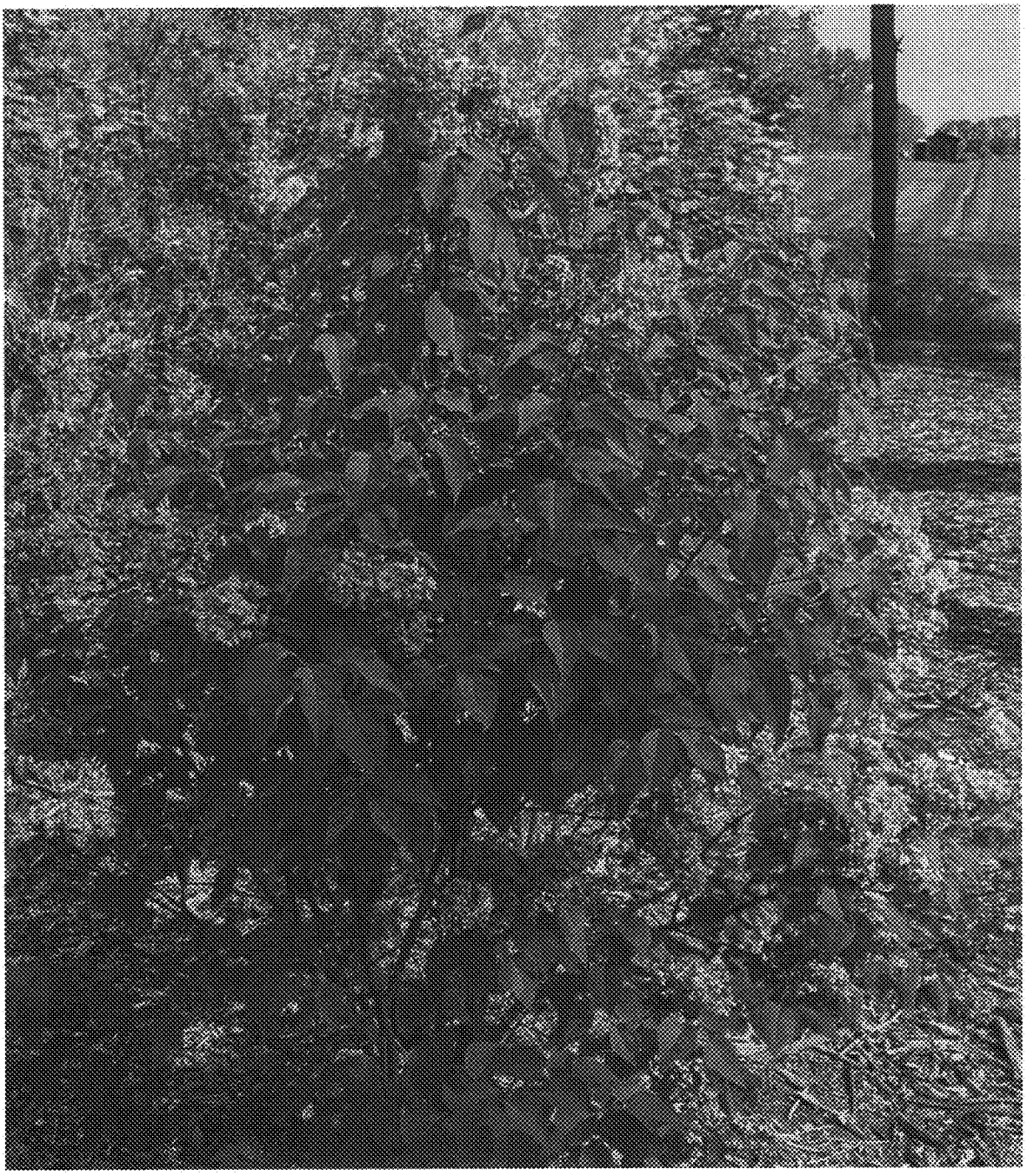
Figure 2:
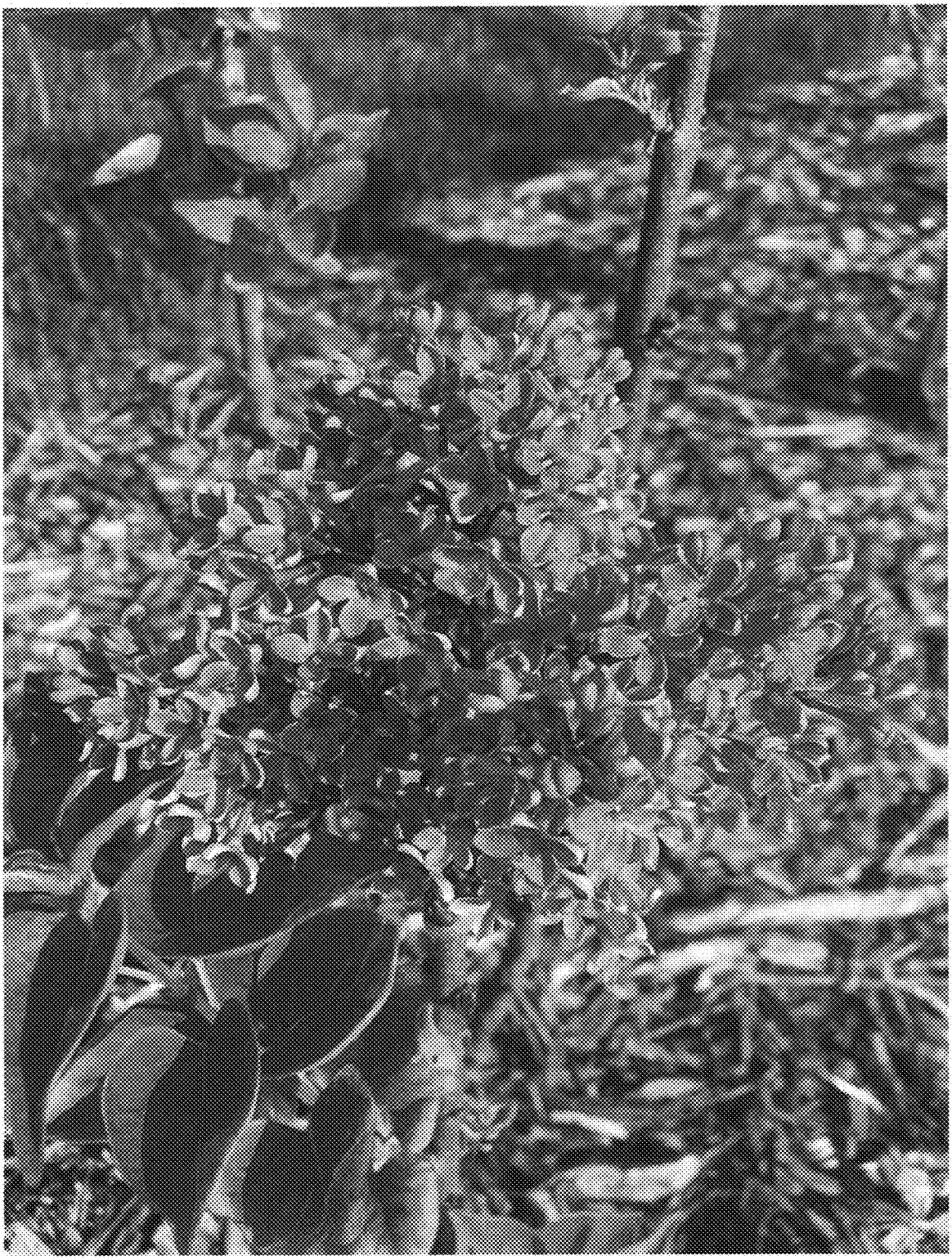

FIG. 1 shows the overall plant habit of 'SCHolirofrag'.
FIG. 2 shows a close-up of the individual flowers, buds, foliage, and bark of the plant.

DETAILED DESCRIPTION

The following detailed descriptions set for the distinctive characteristics of 'SCHolirofrag'. The data which define these characteristics were collected outdoors in Tipp City, Ohio in May 2019 from a 3-year-old plant. The phenotype of this new variety will vary somewhat with variation in environmental, climatic, and cultural conditions as it has not been tested in other environments. Color references are to The R.H.S. Colour Chart of The Royal Horticultural Society of London (R.H.S.) 2001.

Classification:
*Family.*—Oleaceae.
*Species.*—*Syringa hybrida.*
*Common name.*—Lilac.
*Variety.*—'SCHolirofrag'.

Parentage:
*Female parent.*—An un-named and unpatented lilac seedling.
*Male parent.*—'Snowy Beach Party' (unpatented).

Propagation:
*Type.*—Softwood cuttings.
*Time to initiate roots.*—In the summer, 18 to 21 days at 25 degrees Celsius.
*Time to produce a rooted young plant.*—In the summer, 12 to 14 weeks.
*Root description.*—Fibrous.
*Rooting habit.*—Well-branched and dense.

Plant description:
*Plant form and growth habit.*—Upright, dense deciduous shrub or trained as a small tree.
*Branching habit.*—Well-branched, dense.
*Plant height.*—180 cm to 240 cm.
*Plant diameter (area of spread).*—150 cm to 210 cm.

Lateral branch description:
*Length.*—30 cm to 40 cm.
*Diameter.*—4 mm to 5 mm.
*Internode length.*—5 cm.
*Aspect.*—Straight.
*Strength.*—Strong.

*Texture, immature*.—Finely pubescent.
*Texture, mature*.—Becomes rough and woody with age.
*Color, immature*.—RHS 146B.
*Color, mature*.—RHS N200B.

Leaf:
*Arrangement*.—Opposite, simple.
*Length*.—8 cm to 9 cm.
*Width*.—6.5 cm to 7.0 cm.
*Shape*.—Elliptic-ovate.
*Apex*.—Acute.
*Base*.—Cordate.
*Margin*.—Entire.
*Texture*.—Upper surface: Smooth. Lower surface: Smooth mid-rib vein prominent.
*Venation pattern*.—Pinnate.
*Venation color*.—Upper surface: RHS 138D. Lower surface: RHS 147C.
*Immature leaf color*.—Upper surface: RHS 146B. Lower surface: RHS 147C.
*Mature leaf color*.—Upper surface: RHS 137C. Lower surface: RHS 138A.
*Petioles*.—Length: 2.5 cm. Color: RHS 146A. Texture: Smooth.

Flower:
*Flower arrangement and flowering habit*.—Single, salverform, dense, packed in panicles of up to 150 flowers.
*Natural flowering season and flower longevity*.—Mid-spring, 2 to 3 weeks.
*Fragrance*.—Very strong lilac scent.
*Inflorescence height*.—17 cm to 19 cm.
*Inflorescence diameter*.—15 cm to 16 cm.
*Inflorescence shape*.—Conical.
*Flower diameter*.—2 cm.
*Flower length*.—2 cm.
*Flower buds*.—3 mm in diameter, 2 mm long.
*Flower bud color*.—N74B.
*Flower bud texture*.—Smooth.

Petals:
*Quantity*.—Tubular with 4 petal lobes.
*Lobe length*.—10 mm.
*Lobe width*.—6 mm.
*Lobe shape*.—Funnelform.
*Lobe attitude*.—Erect to semi-erect.
*Undulation of lobe*.—Absent.
*Incurving of margin of lobe*.—Medium.
*Apex*.—Rounded.
*Base*.—Fused.
*Margin*.—Entire.
*Texture*.—Upper surface: Smooth, glabrous. Lower surface: Smooth, glabrous.
*Color*.—Upper surface: RHS N74C. Lower surface: RHS 72D.

Sepals:
*Quantity & arrangement*.—Very small and inconspicuous.
*Length*.—1 mm.
*Width*.—1 mm.
*Shape*.—Lanceolate.
*Apex*.—Acute.
*Base*.—Fused.
*Margin*.—Entire.
*Color*.—Upper surface: RHS N77A on side facing sun, shaded side is RHS 146D. Lower surface: RHS 146D.

Peduncles:
*Length*.—6 cm.
*Diameter*.—25 mm.
*Strength*.—Strong.
*Aspect*.—Straight.
*Texture*.—Smooth, glabrous.
*Color*.—RHS 146C.

Pedicels:
*Length*.—3 mm.
*Diameter*.—1 mm.
*Strength*.—Strong.
*Aspect*.—Straight.
*Texture*.—Smooth.
*Color*.—RHS 183A on sun exposed side and RHS 146D on shady side.

Reproductive organs:
*Androecium*.—Quantity of stamens per flower: 2 to 6. Anther shape: Oblong. Anther length: 7 mm. Anther color: RHS 12C. Amount of pollen: Moderate. Pollen color: RHS 28D.
*Gynoecium*.—Quantity of pistils per flower: 1. Pistil Length: 3 mm. Style length: 1 mm. Style color: RHS N155D. Stigma color: RHS 157A. Stigma shape: Oblong. Ovary color: RHS N155D.

Fruit and seed set: None observed.

Disease and insect resistance: Resistant to lilac powdery mildew *Erysiphe syringae* (formerly *Microsphaera syringae* and *Phyllactinia syringae*)

COMPARISON WITH PARENTAL AND COMMERCIAL LINES

Table 1 shows a comparison of differences between 'SCHolirofrag' and both parental lines.

TABLE 1

Comparison with Parental Lines

| Characteristic | 'SCHolirofrag' | Female parent, un-named Lilac seedling | Male parent, 'Snowy Beach Party' |
|---|---|---|---|
| Plant height | 180 cm to 240 cm | 300 cm | 210 cm |
| Plant diameter | 150 cm to 210 cm | 150 cm | 150 cm |
| Flower color, upper surface | RHS N74C | RHS 76A | RHS 155C |
| Flower color, lower surface | RHS 72D | RHS 76B | RHS 155C |

Table 2 shows a comparison of the differences between 'SCHolirofrag' and the commercial Lilac variety 'Yankee Doodle' (unpatented).

TABLE 2

Comparison with Commercial Line

| Characteristic | 'SCHolirofrag' | 'Yankee Doodle' |
|---|---|---|
| Flower color, upper surface | RHS N74C | RHS 77A |
| Flower color, lower surface | RHS 72D | RHS 77B |
| Plant height | 180 cm to 240 cm | 240 cm |
| Plant diameter | 150 cm to 210 cm | 210 cm |
| Flower diameter | 20 mm | 35 mm |

I claim:

1. A new and distinct variety of lilac plant designated 'SCHolirofrag' as illustrated and described herein.

* * * * *